United States Patent [19]

Collins et al.

[11] Patent Number: 4,507,152
[45] Date of Patent: Mar. 26, 1985

[54] FUNGICIDAL AND INSECTICIDAL COMPOSITIONS FOR TREATING WOOD

[75] Inventors: Albert V. Collins, Fairview Park; Richard W. Asmus, Lakewood, both of Ohio

[73] Assignee: Mooney Chemicals, Inc., Cleveland, Ohio

[21] Appl. No.: 557,770

[22] Filed: Dec. 2, 1983

Related U.S. Application Data

[63] Continuation-in-part of Ser. No. 416,101, Sep. 9, 1982, abandoned, which is a continuation-in-part of Ser. No. 386,659, Jun. 9, 1982, abandoned.

[51] Int. Cl.³ ............................................. C09D 5/16
[52] U.S. Cl. ........................... 106/18.31; 106/18.35; 106/18.36; 514/89; 514/514; 514/494; 514/502; 514/503; 514/505; 514/496; 514/498
[58] Field of Search .............. 106/18.31, 18.36, 18.35; 424/289, 287, 295, 293, 291, 296, 200

[56] References Cited

U.S. PATENT DOCUMENTS

| | | | |
|---|---|---|---|
| 2,668,779 | 2/1954 | Herman | 427/323 |
| 2,955,949 | 10/1960 | Kirshenbaum et al. | 106/264 |
| 3,200,003 | 8/1965 | Bescher | 427/325 |
| 3,244,586 | 4/1966 | Rigterink | 424/200 |
| 3,677,805 | 7/1972 | Barnett | 427/325 |
| 3,968,276 | 7/1976 | Allen | 427/297 |
| 4,193,993 | 3/1980 | Hilditch | 424/141 |
| 4,374,852 | 2/1983 | Hilditch et al. | 424/289 |

Primary Examiner—Lorenzo B. Hayes
Attorney, Agent, or Firm—Maky, Renner, Otto & Boisselle

[57] ABSTRACT

An aqueous composition having fungicidal and insecticidal properties is described which is useful particularly for treating wood. The aqueous composition comprises
(a) at least one oil-soluble metal salt of an organic carboxylic acid having fungicidal properties wherein the metal is zinc, chromium, iron, antimony, lead, mercury or a mixture thereof,
(b) at least one halopyridyl phosphate of the formula

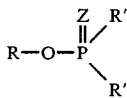

wherein R represents a halopyridyl group, Z represents oxygen or sulfur, and each R' is independently a lower alkoxy, amino or lower alkylamino group,
(c) at least one surfactant, and
(d) from about 60 to 99% of water.

Such compositions penetrate into both dry and green wood rather readily, and the result is wood which is resistant to fungi and insects.

14 Claims, No Drawings

FUNGICIDAL AND INSECTICIDAL COMPOSITIONS FOR TREATING WOOD

CROSS-REFERENCE TO RELATED APPLICATIONS

This application is a continuation-in-part of copending Application Ser. No. 416,101, filed Sept. 9, 1982 which is a continuation-in-part application of copending Application Ser. No 386,659, filed June 9, 1982, both now abandoned.

BACKGROUND OF THE INVENTION

The present invention relates to novel aqueous compositions and particularly to such compositions useful for treating woods to render the wood resistant to fungi and insects. The invention also relates to an inexpensive method for impregnating wood with preservative and fungicidal treatments.

In normal treatments of wood to provide protection against fungus or insect attack, it is common practice to impregnate the wood or timbers with a preservative which is a solution mixture of liquid aromatic hydrocarbons, such as creosote, mixtures of inorganic salts which are dissolved in petroleum distillates. The protection afforded by the application of these materials is dependent upon deep and reasonably uniform penetration into the wood or timber by the preservative material. It also is desirable that the treatment be effective without a significant change in the original dimensions and surface texture of the wood or timbers.

The subject of wood treatment and wood preservation is discussed in some detail in the two-volume treatise entitled "Wood Deterioration and its Prevention by Preservative Treatments", Darrel D. Nicholas, Editor, Syracuse Wood Science Series 5, Syracuse University Press, Syracuse, N.Y., 1973. Among the examples of wood preservatives described therein are various creosote compositions, pentachlorophenol, copper naphthenate, copper-8-quinolinolate, organotin compounds, organomercury compounds, zinc naphthenate, chlorinated hydrocarbons, ammoniacal copper arsenite (ACA), acid copper chromate (ACC), zinc salts such as zinc chloride, zinc oxide and zinc sulfate, chromated copper arsenate (CCA), etc. In Volume II, Chapter 3, pages 279–298, processes and equipment for treating wood are discussed. The pressure treatment is described as the most effective method of protecting wood against attack of decay, insects, fire, etc. Non-pressure treatments also are discussed in this chapter. Dipping is suggested primarily as a satisfactory surface treatment although some penetration is observed. Another non-pressure technique is the diffusion process with unseasoned wood. The author indicates the process requires long treating periods because of slow diffusion rates.

While the literature on the subject of such wood treatments is extensive and covers a period of at least 100 years, most of the procedures which have been described for treating wood with preservatives and resin components, including pressure treatments, do not result in extensive uniform impregnation of the material into the heart of the wood and/or the procedures require a long period to effect the penetration. The problem is particularly acute when treating some types of green or incompletely seasoned wood such as soft pine.

The use of liquid aromatic hydrocarbons for preparing impregnating solutions imparts to the wood strong odors and leaves the wood with a surface which is oily and difficult to paint. Moreover, liquid aromatic hydrocarbons are flammable materials requiring special handling and safety precautions which add to the cost of the wood treatment.

Wood treated with organic preservatives dissolved in petroleum distillates have the same disadvantages as wood treated with the aromatic hydrocarbons. Using lower boiling petroleum distillates, such as mineral spirits, as the solvent, fails to eliminate the disadvantages completely. Prolonged air seasoning after treatment is frequently required to permit sufficient evaporation of the solvent if the wood is to be painted. During this period of air seasoning, a portion of the preservative can migrate to the surface of the wood with the solvent, and thus, the retention of the preservative into the wood is reduced below that contemplated by the treatment.

Regardless of which impregnating solution is employed, the most common commercial procedure for impregnating wood involves subjecting wood to the preservative under relatively high pressures such as 150 to 200 pounds to the square inch for a substantial period of time such as from one hour to 24 hours. The process also may require relatively high temperatures such as from about 75° C. to about 90° to 95° C. Although increases in pressure tend to increase the amount of preservative absorbed by the wood, it may cause the penetration to be erratic or uneven. Moreover, the application of pressure can cause compression of the outer layers of the wood, particularly after wood is weakened and softened by steaming. The collapse of the wood cells is likely to occur especially when relatively soft, unseasoned wood of low specific gravity is being treated. On collapse of the wood cells in an area, there is formed a relatively impenetrable layer which restricts or even completely blocks the flow of preservatives into the interior of the wood.

It also has been suggested to improve the method of pressure treatment by first subjecting the wood to a vacuum treatment. Examples of prior art patents describing methods of impregnating wood utilizing a vacuum followed by pressure include U.S. Pat. Nos. 2,668,779; 3,200,003 and 3,968,276.

U.S. Pat. No. 3,677,805 describes a modification of the pressure treatment. In this procedure, the wood is immersed in a treatment liquid inside a pressure vessel, and the pressure is increased to operating pressure whereupon the contents of the vessel then are subjected to the action of a pulsating pump which provides sinusoidal pressure pulses within the vessel. In other words, pressure pulses are applied repetitively in modulated amplitude to provide variable pressure peaks above and below the ambient pressure maintained in the pressure vessel. This procedure requires equipment which includes a pulsating pump operating into a pressure vehicle equipped with a pressure release means.

The above-described prior art represents a small sampling of the suggestions which have been made for treating wood with preservative materials to prevent decay. In spite of these many suggestions made in the prior art, there continues to be a need for an inexpensive and safe, treatment which is effective and which results in the uniform penetration of the preservatives and other chemicals to the core of the wood.

SUMMARY OF THE INVENTION

A new aqueous composition useful for the preservation of wood and which results in good penetration of the treating of chemicals into the wood is described. More particularly, in accordance with the present invention, an aqueous composition is described having fungicidal and insecticidal properties. Such composition comprises (a) at least one oil-soluble metal salt of an organic carboxylic acid having fungicidal properties wherein the metal is zinc, chromium, iron, antimony, lead, mercury, or a mixture thereof, and (b) at least one halopyridyl phosphate of the formula

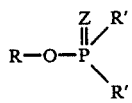

FORMULA I wherein R represents a halopyridyl group, Z represents oxygen or sulfur, and R' is independently a lower alkoxy, amino or lower alkylamino group, (c) at least one surfactant, and (d) from about 60 to 99% of water.

Preferably the aqueous composition will contain a small amount of a hydrocarbon solvent, and the metal salt will be a zinc salt. The invention also includes methods for treating wood with the compositions of the invention including impregnating the wood with the aqueous compositions at either atmospheric pressure or at elevated pressures.

DESCRIPTION OF THE PREFERRED EMBODIMENTS

Many wood preservative chemicals presently available are effective when used alone, but are not always compatible with other materials that are needed in a finished product to provide a system for use as a combination fungicide and insecticide for wood. The present invention utilizes as a fungicide, at least one oil-soluble metal salt of an organic carboxylic acid having fungicidal properties wherein the metal is zinc, chromium, iron, antimony, lead, mercury, or a mixture thereof, and as an insecticide, at least one halopyridyl phosphate having the general Formula I given above. These two classes of chemicals which might be expected, because of their reactive nature, not to be compatible in an aqueous system, have, surprisingly enough, been found to be quite stable when mixed together in various proportions. It also has been found that within a certain range of weight ratios of oil-soluble salt and halopyridyl compound in the presence of a small amount of surfactant and water, the mixture is a clear solution while at other weight ratios, the mixture separates into two phases on standing.

The first essential component of the aqueous compositions utilized in the present invention is at least one oil-soluble metal salt having fungicidal properties wherein the metal is zinc, chromium, iron, antimony, lead, mercury, or a mixture thereof. The oil-solubility of the metal salts of the invention is believed to contribute greatly to the advantageous and desirable results which are obtained. Since the organic compound is oil-soluble and essentially hydrophobic, it therefore, does not have a tendency to be extracted or leached from the treated wood even over an extended period of time.

The preferred metal salts based on stability of the aqueous system are the zinc salts. Particularly preferred types of oil-soluble metal salts which are useful in the aqueous compositions of the present invention are the acid, neutral and basic salts of organic carboxylic acids having from about 6 to 30 carbon atoms. These salts also are known in the art as "soaps".

As mentioned, the salts can be acid, neutral or basic. The acid salts contain an amount of metal cation to neutralize the acid. The neutral salts contain an amount of metal cation just sufficient to neutralize the acidic groups present in the salt anion. The basic salts contain an excess of metal cation and are often referred to as overbased, hyperbased or superbased salts. These acid, basic and neutral salts preferably are of oil-soluble organic carboxylic acids and mixtures of such acids.

The carboxylic acids from which suitable acid, neutral and basic salts can be prepared include aliphatic, cycloaliphatic and aromatic mono-and polybasic carboxylic acids. The organic carboxylic acids can be either natural or synthetic, or mixtures thereof. The examples of natural acids, although usually refined, include straight and branched chain carboxylic acids and mixtures such as tall oil acids and cyclic carboxylic acids such as naphthenic acids. A variety of synthetic carboxylic acids, and particularly aliphatic carboxylic acids or mixtures thereof is useful, and these generally contain six or more carbon atoms.

The metal salts or soaps can be prepared by fusion or precipitation methods. The soaps normally are prepared in an inert liquid medium such as a hydrocarbon oil or solvent. The organic carboxylic acids generally will have at least six carbon atoms and as many as 30 carbon atoms, but when more than one carboxylic acid is employed, carboxylic acids containing as little as two carbon atoms may be employed as one of the acids of the mixture. Examples of useful organic carboxylic acids include acetic acid, propionic acid, butyric acid, isopentanoic acid, hexoic acid, 2-ethyl butyric acid, nonylic acid, decanoic acid, 2-ethyhexoic acid, isooctanoic acid, isononanoic acid, neodecanoic acid, lauric acid, palmitic acid, stearic acid, oleic acid, linoleic acid, naphthenic acid, and commercially available mixtures of two or more carboxylic acids such as naphthenic acid, tall oil acids, rosin acids, etc.

The basic salts or soaps are preferred since these contain higher amounts of metal. For example, solutions of normal zinc salts of monocarboxylic acids such as neodecanoic acid contain about 6% zinc whereas a solution of a basic zinc neodecanoate can contain up to about 16% or more of zinc.

Basic metal salts or soaps of carboxylic acids also can be prepared by methods well known in the art. Examples of neutral and basic salts and of metal salt complexes as well as their preparation can be found in, for example, U.S. Pat. Nos. 2,251,798; 2,955,949; 3,723,152; and 3,941,606 which disclosures are hereby incorporated by reference. Some of the basic salts have been referred to as complexes because they are not simple salts. For example, the basic compositions described in U.S. Pat. No. 3,941,606 are referred to as "metal carboxylate alkoxy alcoholate" complexes. For the purpose of this invention, such basic complexes are to be included in the term metal salts or soaps as used in this specification and claims.

Specific examples of the salts or soaps which are useful in the method of the invention include those described below in Table I and the following specific examples.

TABLE I

Carboxylate Metal Salts

| Component | Metal | Metal Content (%) | Acid |
|---|---|---|---|
| A-1 | Zn | 18 | 2-ethyl hexoic |
| A-2 | Zn | 8 | napthenic |
| A-3 | Zn | 16 | mixture of $C_8$–$C_{13}$ |

The preparation of the above described metal salts is illustrated by the following examples. Unless otherwise indicated, all references to parts and percentages in this application are by weight.

EXAMPLE A-1

A mixture of 628 parts of 2-ethylhexoic acid, 190 parts of mineral spirits, 3 parts of acetic acid and 3 parts of water is charged to a reactor, and the mixture is heated with agitation to a temperature of about 65° C. The mixture is sparged with carbon dioxide, and 233 parts of zinc oxide are added to the mixture, which is then heated to a temperature of about 150° C. The reaction is continued at this temperature while periodic checks are made for percent zinc, base number and percent water. If necessary, the base number is adjusted to 65–80 for 18% zinc content. If the water content exceeds 0.4%, the mixture is dehydrated.

About 8 parts of filter aid are added with stirring to the mixture, which is then filtered. The filtrate is a clear liquid which is adjusted if necessary to a zinc content of 18%, using mineral spirits. The yield is about 1,000 parts.

EXAMPLE A-2

A mixture of 628 parts of distilled naphthenic acid (190 acid number), 300 parts of mineral spirits, 3 parts of acetic acid, 7 parts of water, and 1 part of zinc dust is charged to a reactor, and sparging with carbon dioxide is initiated. The mixture is heated with agitation to a temperature of about 65° C. A gradual addition of 103 lbs. of zinc oxide is made to the mixture, while heating it to a temperature of about 105° C. The reaction is continued at this temperature while periodic checks are made for percent zinc, base number, color and percent water. If the water content exceeds 0.5%, the mixture is dehydrated.

About 4 parts of filter aid are added with stirring to the mixture, which is then filtered. The filtrate is a clear liquid which is adjusted if necessary to a zinc content of 8%, using mineral spirits. The yield is about 1,000 parts of product.

EXAMPLE A-3

A mixture of 355 parts of synthetic neoacids, molecular weight 158–224, 200 parts of 2-ethylhexoic acid, 280 parts of mineral spirits, 29 parts of propionic acid, 10 parts of water and 15 parts of zinc dust is charged to a reactor. The mixture is heated, with agitation and sparging with carbon dioxide. When the batch temperature reaches 65° C., 202 parts of zinc are added, while maintaining the batch temperature at 85° C. maximum. The reaction is continued at this temperature while periodic checks are made on clarified samples for percent zinc and base number. The base number is maintained by adjustment, if necessary, at approximately 68 (at 16% zinc content).

When the reaction is substantially complete, as indicated by the zinc analysis, the mixture is heated to about 105° C. The carbon dioxide sparging is stopped and vacuum is applied until the water content of the mixture is approximately 0.1%.

About 4 parts of filter aid are added with stirring to the mixture, which is then filtered. The filtrate is a clear liquid which is adjusted if necessary to a zinc content of 16%, using mineral spirits. The yield is about 1,000 parts of product.

Carboxylate metal salts of the type described above are available commercially such as from Mooney Chemicals, Inc., Cleveland, Ohio, 44113 under the general trade designations TEN-CEM, CEM-ALL, NAP-ALL, HEX-CEM, LIN-ALL, and NEO-NAP. These mineral spirit solutions can be adapted for use in preparing the aqueous systems of the present invention by adjusting the mineral spirits content (generally reducing the amount of mineral spirits) and mixing said mineral spirit solutions with water and surfactants as described below.

Water dispersable solutions/dispersions of metal salts also are available from Mooney Chemicals, Inc. under the general trade designation HYDRO-NAP ™. The metal content of these salts also ranges from about 4% to about 10%, but these solutions/dispersions already contain the desired surfactants and can be readily mixed with water to form the desired aqueous systems. Mixtures of the carboxylic acid salts such as those described in Table I are easily prepared and utilized in accordance with the invention.

Examples of other neutral and basic salts include lead naphthenate, lead neodecanoate, lead 2-ethyl hexoate, lead tallate, zinc tallate, chromium 2-ethyl hexoate, chromium tallate, chromium oleate, antimony octoate, antimony oleate, iron naphthenate, iron tallate, phenyl mercury oleate, mercury dioleate, etc.

The aqueous compositions of the invention, in addition to the metal salts and soaps described above, also contain a halo-pyridyl phosphate having the formula

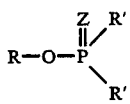

FORMULA I wherein R represents a halopyridyl group, Z represents oxygen or sulfur, and each R' is independently a lower alkoxy, amino or lower alkyl amino group. In the present specification and claims, the terms lower alkoxy and lower alkyl are intended to include groups containing from one to about eight carbon atoms. The halopyridyl phosphates utilized in the compositions of the invention generally are solid or viscous liquid materials which exhibit fairly low solubility in water.

In Formula I, R' preferably is a lower alkoxy group such as methoxy, ethoxy, isopropoxy, butoxy, etc. Although the two R' groups may be different, they generally are the same and preferably alkoxy groups. Examples of the R group, or halopyridyl group, include mono-, di- and trihalo-pyridyl groups, but preferably the dichloro and trichloro derivatives. Specific examples of the halopyridyl groups include 3,5-dichloro pyridyl; 3,5,6-trichloro pyridyl; 3,5-dibromo-6-chloro pyridyl; 5,6-dichloro pyridyl, etc.

Specific examples of the halopyridyl phosphate included in the composition of the invention include the following: O,O-diethyl-O-(3,5,6-trichloro-2-pyridyl)-phosphorothioate; O-methyl-O-3,5,6-trichloro-2-pyridyl isopropyl-phosphoramidothioate; O-isopropyl-O-

3,5-dichloro-2-pyridyl methyl phosphoramidothioate; O,O-diethyl-O-3,5-dibromo-6-chloro-2-pyridyl phosphorothioate, etc.

The halopyridyl phosphates useful in the present invention are described in U.S. Pat. No. 3,244,586, and the procedures for preparing such compounds are described in the patent. In a preferred method, the compounds are prepared by reacting a phosphorochloridate or phosphorochlorodothioate having the formula

 FORMULA II with an alkali metal or tertiary amine salt of a halopyridinol having the formula

wherein R, Z and R' are as defined in Formula I. The reaction is carried out conveniently in an inert organic solvent such as acetone, dimethylformamide, carbon tetrachloride, chloroform, benzene, toluene, etc. The amounts of the reagents to be employed are not critical, but in a preferred method of operation, excellent results are obtained when employing substantially equimolar proportions of the pyridinol salt and phosphorochloridate or phosphorochlorodothioate. The reaction occurs at temperatures in the range of from about 0° to 100° C. with the production of the desired product and a chloride by-product. In carrying out the reaction, the reactants are mixed and contacted together in any convenient fashion and the resulting mixture maintained for a period of time at the desired reaction temperature to complete the reaction. Following completion of the reaction, the mixture is washed with water and any organic reaction medium being removed by fractional distillation, generally at reduced pressure to obtain the desired product as residue. The product can be further purified by conventional procedures such as washing with water.

Alternate procedures for preparing such compounds are described in U.S. Pat. No. 3,244,586, and it is not believed necessary to unduly lengthen this disclosure by further description of the preparation of such compounds.

Some of the halopyridyl phosphates which can be utilized in the compositions of the invention are available commercially such as from the Dow Chemical Company. One preferred halopyridyl phosphate compound which is useful in the compositions of the invention is available commercially from Dow under the general trade designation Dursban. The Dursban material also is known as chlorpyrifos. Chemically, the compound is identified as O,O-diethyl-O-(3,5,6-trichloro-2-pyridyl)phosphorothioate. Dursban A is 94% active while Dursban TC concentrate is a 42% active water-dispersable solution.

The aqueous compositions of the invention also contain at least one surfactant. These surfactants can be incorporated into the aqueous compositions of the invention by first preparing mixtures of said surfactants with either or both of the above ingredients, namely, the metal salts and halopyridyl phosphate compounds, or the surfactants can be incorporated into the compositions of the invention when the concentrates are diluted with additional water. Preferably, the surfactants are anionic or nonionic surfactants. Many such surfactants are known in the art. See, for example, McCutcheon's "Detergents and Emulsifiers", 1979, North American Ediion, published by McCutcheon's Division, MC Publishing Corporation, Glen Rock, N.J., U.S.A., particularly pages 15–20 which are hereby incorporated by reference for their disclosure in this regard.

In general, the nonionic surfactants such as those containing ether linkages are particularly useful. Examples of such ether-containing surfactants are those having the general formula $$R_1-O-[(CH_2)_nO]_xH$$

wherein $R_1$ is an aryl or alkyl group containing from about 6 to 20 carbon atoms, n is two or three, and x is an integer between 2 and 100. Such surfactants are produced generally by treating fatty alcohols or alkylsubstituted phenols with excess ethylene oxide or propylene oxide. The alkyl carbon chain may contain from about 14 to 24 carbon atoms and may be derived from a long chain fatty alcohol such as oleyl alcohol or stearyl alcohol.

Nonionic polyoxyethylene compounds of this type are described in U.S. Pat. No. 3,855,085. Such polyoxyethylene compounds are available commercially under the general trade designations "Surfynol" by Air Products and Chemicals, Inc. of Allentown, Pa., and under the designation "Pluronic" or "Tetronic" by BASF Wyandotte Corp. of Wyandotte, Mich. Examples of specific polyoxyethylene condensation products include "Surfynol 465" which is a product obtained by reacting about ten moles of ethylene oxide with one mole of tetramethyldecynediol. "Surfynol 485" is the product obtained by reacting 30 moles of ethylene oxide with tetramethyldecynediol. "Pluronic L 35" is a product obtained by reacting 22 moles of ethylene oxide with polypropylene glycol obtained by the condensation of 16 moles of propylene oxide. Also useful is Atlox 1045A from ICI America, Inc. which is a polyoxyalkylene sorbitol oleate-laurate mixture.

Amine, long chain fatty amine, long chain fatty acid, alkanol amines, diamines, amides, allkanol amides and polyglycol-type surfactants known in the art are also useful. One type found particularly useful is the group obtained by the addition of a mixture of propylene oxide and ethylene oxide to diamines. More specifically, compounds formed by the addition of propylene oxide to ethylene diamine followed by the addition of ethylene oxide are useful and are available commercially from BASF Wyandotte, Inc., Chemical Group under the general trade designation "Tetronic".

Carbowax-type wetting agents which are polyethylene glycols having different molecular weights have been found to give good results. For example, Carbowax No. 1000 has a molecular weight range of from about 950 to 1050 and contains from 20 to 24 ethoxy units per molecule. Carbowax No. 4000 has a molecular weight range of from about 3000 to 3700 and contains from 68 to 85 ethoxy units per molecule. Other known nonionic glycol derivatives such as polyalkylene glycol ethers and methoxy polyethylene glycols which are available commercially can be utilized as surfactants in the compositions of the invention.

Anionic surfactants also are useful in the aqueous compositions of the invention. Among the useful anionic surfactants are the widely-known metal carboxylate soaps, organo sulfates, sulfonates, sulfocarboxylic acids and their salts, and phosphates. Various anionic surfactants are readily available commercially, and further information about anionic surfactants can be found in the text "Anionic Surfactants" Parts II and III, edited by W. M. Linfield, published by Marcel Dekker, Inc., New York, 1976. Examples of anionic surfactants available from ICI America, Inc. include Atlas G-2205 which is an aromatic phosphate and Atlas G-3300 which is an alkyl aryl sulfonate. Examples of anionic surfactants available from Rohm and Haas Company include Triton 770 which is a sodium salt of an alkyl aryl polyether sulfate, Triton GR-5M which is a dioctyl sodium sulfosuccinate, Triton H-55 which is a phosphate surfactant, potassium salt, Triton W-30 and Triton X-200 which are sodium salts of alkyl aryl polyether sulfonates, etc.

Mixtures of the nonionic and anionic surfactants can and are generally utilized in the aqueous systems of the present invention. The amount of surfactant contained in the aqueous mixture can vary over a wide range, but is generally from 0.25% to about 7.5% and more preferably between 1% and 5%.

In addition to the metal salts and soaps, the halopyridyl phosphate compounds, and the surfactants, the aqueous compositions utilized in the method of the invention also contain water. The amount of water generally will be from about 60 to 99% by weight and more generally between about 60 to 90%. The aqueous compositions of the invention either are solutions or stable dispersions or emulsions.

The weight ratios of metal salt to halopyridyl phosphate in the aqueous compositions of the invention can vary over a wide range depending on the results desired and the anticipated end use for the wood. Generally, the weight ratio of metal salt to phosphate can vary from about 99:1 to 1:99, and a preferred weight ratio is from about 30:1 to 5:1. In general the aqueous compositions of this invention comprise (a) about 0.1 to 25% of at least one oil-soluble metal salt of an organic carboxylic acid,
(b) about 0.05 to 15% of the halopyridyl phosphate,
(c) about 0.25 to 7.5% of at least one surfactant,
(d) about 60 to 99% of water, and
(e) less than about 20% of an organic solvent.

The aqueous compositions appear to be substantially stable (i.e., little or no apparent reaction between the metal salt and phosphate compound or degradation of the phosphate compound) for extended periods although some coloration appears on prolonged standing. Stable single phase compositions can be prepared from mixtures of commercially available Dursban TC and zinc HYDRO-NAP.

As noted above, the aqueous compositions of the present invention generally contain less than about 20% of hydrocarbon solvents. Preferably, the amount of hydrocarbon solvent contained in the aqueous mixture is maintained at a minimum and will generally be less than about 15% of the aqueous system.

The aqueous compositions of the present invention can be prepared by mixing the metal salt, insecticide and the surfactants with sufficient water to provide the desired levels of ingredients. Alternatively, and more preferably, the aqueous compositions are prepared from water-dispersable additive concentrates of the metal salt, and concentrates of insecticides which also may contain one or more surfactants, water and optionally a hydrocarbon solvent.

Aqueous additive concentrates of metal salts, surfactants and hydrocarbon solvents are available commercially from Mooney Chemicals, Inc. under the general trade designation HYDRO-NAP. Moreover, water-dispersable additive concentrates can be prepared from commercially available solutions of metal salts and mineral spirits by blending the mineral spirit solutions with the desired surfactants with or without additional hydrocarbon solvents such as mineral oils. For example, a water-dispersable additive concentrate can be prepared from the metal salt solutions in mineral spirits illustrated above as Examples A-1 to A-3 by thoroughly mixing the mineral spirit solutions with mineral oil and surfactants.

The diluted aqueous compositions useful for treatment of wood in accordance with the invention preferably can be prepared by mixing an aqueous concentrate of insecticide and an aqueous concentrate of the metal salt in the presence of the desired amount of water and surfactant to form the wood-treating mixture.

The aqueous compositions of the present invention also may contain other additives which impart desirable properties to the treated wood. For example, the aqueous systems of the invention may contain flame retardant compositions, coloring agents and odorants. Generally, these additives can be included in the concentrates or in aqueous compositions of the invention in the disperse phase or dissolved in the water. The amount of such additives included in the aqueous compositions of the invention may vary over a rather wide range although amounts of from about 0.5 to about 5% of these compositions generally is satisfactory.

Inorganic fire retardant compositions are particularly useful in the aqueous compositions of the invention. Examples of inorganic materials include diammonium phosphate, monoammonium phosphate, ammonium chloride, ammonium sulfate, borax and zinc chloride. Examples of organic fire retardants include a number of halogenated and organo-phosphorus compounds which either may be dispersed in the aqueous systems as mentioned above or rendered soluble by forming water-soluble salts or solutions of the fire retardants which can then be mixed with the water-dispersable additive concentrates or the aqueous systems of the invention. For example, ammonium salts of organo-phosphorus compounds may be employed in the aqueous compositions of the invention. In particular, examples include ammonium salts of bis-dibromo propyl phosphate, diethyl phosphate, bis(beta-chloroethyl)phosphate, bis(1,3-dichloropropyl)phosphate, etc. Other water-soluble organic fire retardants include aliphatic carboxylic acids containing over 50% organically bound bromine, alkyl sulfamates, ammonium alkyl phosphates, antimony trichloride with tertiary amines such as ethanol amines, urea with ammonium phosphate and urea with sulfamic acid.

Although various types of wood which can be treated in accordance with the method of the invention generally have a satisfactory appearance for most purposes, the appearance can be modified if desired by imparting different color effects. The present invention contemplates the inclusion in the aqueous compositions of coloring agents which either are soluble or dispersable in the aqueous systems of the invention. Any of the known oil-soluble, water-soluble or water-dispersable coloring agents can be used. These agents are mixed either with the water-dispersable additive concentrates of metal salts described above, or the diluted aqueous compositions, and when the wood is immersed in the aqueous compositions of the invention containing coloring agents, the coloring agents penetrate the wood with the metal salts give desirable coloring effects which in some instances emphasize the grain of the wood. Examples of coloring agents which may be used depending on the desired results include: Bruco Creosote Brown RGY available from Bruce Chemical Co., Iron CEM-ALL available from Mooney Chemical, Inc., and Pylaklor Red Brown LX-6249 available from Pylam Dye Co.

Odorants can be included in the aqueous compositions of the invention. A particularly effective and desirable odorant is pine oil. Other water-soluble or dispersable compounds having desirable odors can be included in the concentrates or diluted aqueous composition.

The process of this invention involves contacting the wood with the aqueous compositions for a period of time sufficient to enable the desired amount of metal salt and insecticide to penetrate into the wood. Contact between the wood and the aqueous compositions can be effected by brushing, spraying, painting, immersion, etc. One of the surprising features and advantages of the present invention is that excellent results have been obtained when green wood is contacted at atmospheric pressure in aqueous systems containing as little as 2% of zinc or 0.2% of the insecticide for periods of as little as five to ten minutes. Moreover, subsequent analysis of the green wood treated in accordance with this procedure reveals an excellent zinc salt and insecticide pick-up with exceedingly good penetration of the materials into the wood.

In one method of the present invention, the aqueous composition in which the green wood is immersed can be maintained at a temperature of from about 5° to about 95° C. However, the method of the invention can be, and is preferably carried out at ambient temperature thereby eliminating the need for any equipment or materials for heating or cooling the aqueous systems. In some instances, it may be advantageous to heat the aqueous systems to elevated temperatures to increase the rate of penetration.

As mentioned above, after the green wood has been immersed in the aqueous systems of the present invention for the desired period of time, the wood is removed from the aqueous system. The thus treated green wood is ready for shipping, although it may be desirable in some instances to allow the wood to at least partially dry before shipping.

It is surprising that desirable results can be obtained with such short contact times of the wood and aqueous compositions. It is believed that the aqueous compositions used in this invention deposit the desired amount of material on and in the outer layers of the wood during the brief contact to provide the desired results even though the metal salts and other additives have not completed the penetration process into the wood. After the treated logs are removed from contact with the aqueous composition, the salts and other additives continue to penetrate into the wood while the wood is in storage or in shipment. Accordingly, this invention provides a method for treating wood which not only uses inexpensive equipment (such as a large open tank), but a method by which the wood to be treated is in the equipment for short periods of time.

The method of the invention also can be conducted on wood contained in an enclosed vessel under vacuum or pressure conditions or a combination thereof. The use of pressure for improving the penetration of various chemicals into all types of wood is well known in the art. In this technique, the wood, either dry or fresh cut and green is placed in a chamber which is sealed and evacuated in a regulated cycle which is related to and determined from a consideration of the species of wood. Generally, the period of evacuation will vary from about 15 minutes to one hour and the pressure within the sealed chamber is brought to a level of about two inches of mercury or less. The purpose of this step is to remove air and wood volatiles from the wood. The diluted aqueous compositions of the invention then are introduced into the enclosed container, and the amount of composition should be sufficient to immerse the wood completely. Pressurization of the vessel is then initiated and the pressure maintained at a desired level for a given period of time. Initially, the pressure within the vessel will decrease as the aqueous composition within the container penetrates into the wood. The pressure can be raised to maintain a desirable level throughout the penetration period of treatment. Stabilization of the pressure within the vessel is an indication that there is no longer any penetration of the liquid into the wood. At this point, the pressure can be released, the vessel drained, and the wood removed.

The details of the pressure process, including pressure ranges, concentration of aqueous composition and the cycling of vacuum and pressure with respect to a particular species of wood can be readily determined by one skilled in the art from the examples which follow and also by following the procedure of this invention on the particular wood while varying process parameters to provide optimum results. For example, the pressures utilized in the above-described pressure method can be as high as 300 psig., and are generally from about 50 to 250 psig.

The method of the invention can be carried out on a wide variety of wood types. The actual time of immersion of the wood in the aqueous compositions of the invention will vary depending on (1) whether the immersion of the wood is at atmospheric pressure or at elevated pressures as described above, (2) the amount of metal salt and insecticide to be introduced into the wood, and (3) the difficulty of penetration into the particular type of wood being treated. Any type of wood, dry or green, can be treated with the compositions of the invention. Green wood generally is defined as wood containing 30% or more by weight of water. Dry wood is defined as wood containing less than 30% by weight of water based on bone dry wood. Specific examples of wood specifies which can be treated in accordance with the method of the invention include Western Red Cedar, Douglas Fir, Inland Fir, Spruce, Hemlock, Sugar Maple, Ash, Walnut, White Oak, Cherry, White Pine, Red Pine, Birch, Red Oak, Elm, Hickory, Linden, Beach, Sycamore, etc.

The following are specific examples of the compositions of the invention.

EXAMPLE 1

An aqueous composition comprising 5.2 kg. of 8% zinc HYDRO-NAP, 56 grams of pine oil, 230 grams of Dursban TC, and 48.5 gal. of water is prepared. The mixture is clear and stable and contains about 0.22% of zinc and 0.1% of O,O-diethyl-O-(3,5,6-trichloro-2-pyridyl)phosphorothioate.

EXAMPLE 2

An aqueous composition is prepared comprising 5.2 kg. of 8% zinc HYDRO-NAP, 56 grams of pine oil, and 470 grams of Dursban TC diluted to 50 gallons with water. The mixture is stable and contains about 0.22% of zinc and 0.3% of the phosphorothioate.

EXAMPLE 3

An aqueous composition is prepared comprising 5.2 kg. of 8% zinc HYDRO-NAP, 56 grams of pine oil, and one kilogram of Dursban TC diluted to 50 gallons with water. This composition contains about 0.22% of zinc and 0.5% of the phosphorothioate.

EXAMPLE 4

An aqueous composition is prepared by mixing 8% zinc HYDRO-NAP and Dursban TC insecticide with water and stirring to provide a mixture containing about 2.67% zinc and 3.6% of the phosphorothioate of Example 1. This aqueous composition which is more concentrated than the above examples is useful for impregnating wood at atmospheric pressure.

As mentioned above, the aqueous compositions of this invention, especially those containing a zinc salt such as illustrated in Examples 1–4, are relatively stable for long periods of time. Contrary to expectations, the metal salts and the halopyridyl phosphate can be mixed in the water and there is little degradation of the phosphate, even on prolonged standing. It has been reported previously that copper carboxylates, and possibly other heavy metal carboxylates, will promote the degradation of halopyridyl phosphates to a pyridinol product and other degradation products which are inactive as insecticides.

The method of the present invention for treating wood can be illustrated with the following examples. As it is mentioned above, the method of the invention can be conducted either at atmospheric pressure or at elevated pressures.

EXAMPLE A

This example illustrates the method of the invention conducted at atmospheric pressure. Logs (partially debarked and green) are immersed in the aqueous composition of Example 4 maintained at ambient temperature, and the wood logs are maintained in the composition for about six minutes. The logs then are removed from the aqueous compositions and allowed to drip dry. Examination of the log specimens treated in accordance with this procedure shows a satisfactory zinc and phosphorothioate pick-up and retention. On standing, the penetration of the material into the wood continues.

EXAMPLE B

This example illustrates an embodiment of the invention utilizing pressure. About 66 pounds of red pine logs cut to six-foot lengths are placed in a suitable chamber which is then closed. A vacuum is supplied and maintained for about 30 minutes whereupon the aqueous composition of Example 2 is admitted into the vessel. When all of the aqueous composition is in the vessel, pressurization of the vessel up to about 250 psig. is begun. When the internal pressure begins to decrease, indicating penetration and absorption of the solution by the logs, the pressure is raised again to 250 psig. to maintain the desired positive pressure. After a period of about 30 to 45 minutes, the pressure is stabilized that no additional aqueous composition is penetrating into the wood. The pressure is released, the chamber is drained and the logs removed. The logs treated in this manner (representing about 18 board feet) weighed 89 pounds indicating a pick-up of 0.034 pounds per cubic foot of zinc, and 0.047 pounds per cubic foot of the phosphorothioate.

EXAMPLE C

About 70 pounds of red pine logs (partially debarked, green and about six-feet long) are placed in a suitable vessel which is closed and evacuated. The aqueous composition prepared in Example 3 is introduced into the vessel and pressurization is begun to a level of 250 psig. As the pressure drops indicating penetration of the solution into the wood, the pressure is raised back to the initial level of about 250 psig. and the procedure is repeated as described in Example B. After about 35 minutes, the pressure is stabilized indicating that no additional penetration of solution into the wood. The pressure is released, the vessel drained and the logs removed. The logs treated in this manner weighed 90 pounds indicating a pick-up of about 20 pounds of aqueous composition. Since about 18 board feet of the logs were treated in this example, the method results in a pick-up of about 0.029 pounds of zinc per cubic foot and 0.0347 pounds of the phosphorotioate per cubic foot.

The embodiments of the invention in which an exclusive property or privilege is claimed are defined as follows:

1. An aqueous composition having fungicidal and insecticidal properties comprising
   (a) at least one oil-soluble metal salt of an organic carboxylic acid having fungicidal properties wherein the metal is zinc, chromium, iron, antimony, lead, mercury, or a mixture thereof, and
   (b) at least one halopyridyl phosphate of the formula

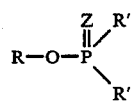

FORMULA I wherein R represents a halopyridyl group, Z represents oxygen or sulfur, and R' is independently a lower alkoxy, amino or lower alkylamino group,
   (c) at least one surfactant, and
   (d) from about 60 to 99% of water.

2. The aqueous composition of claim 1 wherein the composition comprises,
   (a) about 0.1 to 25% of at least one oil-soluble metal salt of an organic carboxylic acid wherein the metal is zinc, chromium, iron, antimony, lead, mercury, or a mixture thereof,
   (b) about 0.05 to 15% of the halopyridyl phosphate,
   (c) about 0.25 to 7.5% of at least one surfactant,
   (d) about 60 to 99% of water, and
   (e) less than about 20% of an organic solvent.

3. The aqueous composition of claim 1 wherein the metal of the metal salt (a) is zinc.

4. The aqueous composition of claim 1 wherein the acid of the metal salt (a) is at least one aliphatic or alicyclic monocarboxylic acid containing from about 6 to about 30 carbon atoms.

5. The aqueous composition of claim 4 wherein the metal salt is a zinc salt.

6. The aqueous composition of claim 1 wherein each R' in the halopyridyl phosphate is a lower alkoxy group.

7. The aqueous composition of claim 6 wherein the halopyridyl phosphate is O,O-diethyl-O(3,5,6-trichloro-2-pyridyl)phosphorothioate.

8. The aqueous composition of claim 1 wherein the weight ratio of metal salt to phosphate is in the range of from 99:1 to 1:99.

9. The aqueous composition of claim 1 wherein the surfactant is an anionic or nonionic surfactant or a mixture thereof.

10. The aqueous composition of claim 1 also containing an odorant.

11. An aqueous composition comprising
(a) at least one oil-soluble acid, neutral or basic zinc salt of one or more organic carboxylic acids having fungicidal properties,
(b) at least one halopyridyl phosphate of the formula

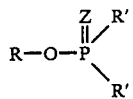

wherein R represents a halopyridyl group, Z represents oxygen or sulfur, and each R' is independently a lower alkoxy, amino or lower alkylamino group,
(c) from about 0.25 to 7.5% of at least one surfactant,
(d) from about 60 to 90% of water, and
(e) less than 15% of a hydrocarbon solvent.

12. The aqueous composition of claim 11 wherein the weight ratio of (a) to (b) is from about 99:1 to about 1:99.

13. The aqueous composition of claim 11 wherein the salt of (a) is a basic zinc salt of at least one aliphatic or alicyclic monocarboxylic acid containing from about 6 to 30 carbon atoms.

14. The aqueous composition of claim 11 wherein the surfactant is an anionic or nonionic surfactant, or a mixture thereof.

* * * * *